United States Patent [19]
Ellis et al.

[11] Patent Number: 6,008,037
[45] Date of Patent: Dec. 28, 1999

[54] USE OF WATER SOLUBLE ENZYME-POLYMER CONJUGATES FOR CLEANING CONTACT LENSES

[75] Inventors: Edward James Ellis, Lynnfield, Mass.; Edwin Georg Emil Jahngen, Kingston, N.H.; Arthur John Meuse, Lynnfield, Mass.

[73] Assignee: Polymer Technology Corporation, Wilmington, Mass.

[21] Appl. No.: 08/964,261

[22] Filed: Nov. 4, 1997

Related U.S. Application Data

[60] Provisional application No. 60/030,899, Nov. 14, 1996.

[51] Int. Cl.$^6$ ........................................... C12S 9/00
[52] U.S. Cl. ........................... 435/264; 435/177; 435/180; 510/114; 514/839
[58] Field of Search ..................................... 435/174–181, 435/188, 263, 264; 510/114; 514/839, 840; 134/901

[56] References Cited

U.S. PATENT DOCUMENTS

| | | |
|---|---|---|
| 3,634,258 | 1/1972 | Wildi et al. . |
| 3,910,296 | 10/1975 | Karageozian et al. . |
| 4,088,538 | 5/1978 | Schneider . |
| 4,096,870 | 6/1978 | Manfuso . |
| 4,179,337 | 12/1979 | Davis et al. ............................ 435/181 |
| 4,710,313 | 12/1987 | Miyajima et al. . |
| 5,080,891 | 1/1992 | Saifer et al. ............................ 424/78.3 |
| 5,122,614 | 6/1992 | Zalipsky ................................ 548/520 |
| 5,133,968 | 7/1992 | Nakayama et al. ..................... 424/401 |
| 5,219,564 | 6/1993 | Zalipsky et al. ...................... 424/78.17 |
| 5,230,891 | 7/1993 | Nakayama et al. ..................... 424/401 |
| 5,324,844 | 6/1994 | Zalipsky ................................ 548/520 |
| 5,349,001 | 9/1994 | Greenwald et al. .................... 525/408 |
| 5,405,877 | 4/1995 | Greenwald et al. ................. 514/772.3 |
| 5,455,027 | 10/1995 | Zalipsky et al. ...................... 424/78.17 |
| 5,705,153 | 1/1998 | Shorr et al. . |
| 5,807,942 | 9/1998 | Sakaki et al. ........................ 526/238.1 |

FOREIGN PATENT DOCUMENTS

| | | | |
|---|---|---|---|
| 0223479 | 5/1987 | European Pat. Off. | .......... A61L 2/18 |
| 0256127 | 2/1988 | European Pat. Off. | .......... C12N 9/00 |
| 0641859 | 3/1995 | European Pat. Off. | ........ C12N 11/14 |
| 93/15189 | 8/1993 | WIPO | .............................. C12N 9/96 |
| 93/20838 | 10/1993 | WIPO | ............................ A61K 37/62 |
| 94/10191 | 5/1994 | WIPO | .............................. C07K 3/06 |
| 96/17929 | 6/1996 | WIPO | .............................. C12N 9/96 |

OTHER PUBLICATIONS

"A Dextran–Protease Conjugate for Cosmetic Use", Ohta, et al., *Cosmetics & Toiletries* Magazine/79, vol. 111, Jun. 1996.

*Primary Examiner*—William H. Beisner
*Attorney, Agent, or Firm*—Chris P. Konkol; Denis A. Polyn; John E. Thomas

[57] ABSTRACT

There are disclosed compositions and methods for cleaning contact lenses using water soluble enzyme-polymer conjugates. A preferred method includes providing the subject enzyme-polymer conjugates in a tablet form, dissolving the tablet in an aqueous solution and subsequently soaking a contact lens in the resulting solution. Other methods include providing the enzyme-polymer conjugate in a liquid form and contacting a contact lens therewith.

4 Claims, No Drawings

USE OF WATER SOLUBLE ENZYME-POLYMER CONJUGATES FOR CLEANING CONTACT LENSES

This application claims the benefit of U.S. Provisional Application No. 60/030,899 filed on Nov. 14, 1996.

FIELD OF THE INVENTION

The present invention generally relates to the use of enzymatic materials for cleaning and removing deposits from contact lenses. The present invention specifically utilizes water soluble enzyme-polymer conjugates for this purpose.

BACKGROUND

The use of enzymes for cleaning and removing organic debris (e.g. protein, lipids, etc.) from contact lenses is well known in the art. Common classes of such enzymes include proteases and lipases. Specific examples of enzyme cleaners are available from Bausch & Lomb, e.g. ReNu® Effervescent Enzymatic Cleaner for soft contact lenses. This cleaner comprises a tablet containing a proteolytic enzyme (subtilisin), polyethylene glycol, sodium carbonate, sodium chloride and tartaric acid. One cleaning regime comprises dissolving the tablet in ReNu® Multi-Purpose Solution or a sterile saline solution in a vial and soaking a soft contact lens in the solution for at least fifteen minutes. Other enzyme cleaners are also commonly used. For example, liquid enzymatic cleaners have been widely available in Japan for cleaning RGP and hard contact lenses.

Enzymes must be thoroughly rinsed from contact lenses after cleaning and before insertion as the enzymes can cause discomfort if applied to the eye. Unfortunately, enzymes can be difficult to remove from many contact lenses. For example, hydrogel lenses are porous and include a large amount of bound water. Enzymes readily penetrate the pores of these lenses and can associate with the bound water therein, making enzyme removal difficult. With respect to RGP lenses, these lenses commonly have an anionic surface which can attract enzymes and can make enzyme removal difficult. If not removed from the lens after cleaning, enzymes can subsequently be released from the lens and into the eye causing stinging and irritation.

Although enzyme cleaners are effective in removing deposits and debris from contact lenses, their continued association with lenses after cleaning and rinsing causes eye irritation and discomfort. It is desired to provide enzyme cleaners that are more easily removed from a lens following cleaning.

SUMMARY OF THE INVENTION

The present invention includes compositions and methods for cleaning contact lenses by contacting a lens with a water soluble enzyme-polymer conjugate. The enzyme-polymer conjugate is easily removed from the lens surface following cleaning, thus reducing eye irritation and discomfort associated with exposure to the enzyme.

DETAILED DESCRIPTION OF THE INVENTION

As indicated above, the present invention includes compositions and methods for cleaning contact lenses with water soluble enzyme-polymer conjugates. Enzyme-polymer conjugates are commercially available or can be synthesized for a particular application using known techniques. Examples of such conjugates are available from Sigma Chemical Company, e.g. Protease Type X (thermolysin) attached to poly(N-methacryloyl-D-glycosamine, and Protease Type XXVII (nagarse) attached to poly(N-methacryloyl-D-glycosamine. Other examples (dextran and polyethylene oxide—protease conjugates) and their preparation are described in: Ohta, et al., *A Dextran-Protease Conjugate for Cosmetic Use*, Cosmetics & Toiletries magazine/79, volume 111, June 1996. These water soluble enzyme-polymer conjugates are known for their improved stability and have been used in cosmetic applications for removing excess stratum corneum cells. Still further applicable preparation techniques are provided in U.S. Pat. Nos. 5,122,614; 5,219,564; 5,324,844; 5,349,001; 5,405,877; and 5,455,027.

The applicable polymers for use in the subject invention are not specifically limited, although such polymers should be water soluble and be capable of forming covalent bonds with desired enzyme molecules. The requirement of water solubility may limit the applicable molecule weight of some polymers. Applicable polymers include both homopolymers and copolymers. Examples of preferred water soluble polymers include: polyvinyl alcohol, polyacrylamides, polyethylene oxide, polyamides e.g. poly N-(2-hydroxypropyl) methacrylamide, and polysaccharides e.g. cellulose, starch, dextran amlose, glycogen, chitin, etc.

The polymers applicable to the present invention may include a variety of monomeric units for modifying the proportions of the overall polymer and enzyme conjugate. For example anionic monomers such as the salts of: acrylic acid, methacrylic acid, 2-acrylamido-2-methyl propanesulfonic acid, and 4-styreresulfonic acid may be copolymerized within the subject polymeric system. Similarly, cahonic monomers may also be copolymerized within the subject polymer. Examples include: 2-acryloxytrimethylammonium chloride and 3-methacryloxy-2-hydroxypropyltrimethylammonium chloride. As yet another example, neutral monomers such as hydroxyethylmethacrylate, N-vinylpyrrolidone and glycerol mono(meth)acrylate may be copolymerized within the subject polymer system.

The applicable enzymes for use in the present invention are not specifically limited, but must remain active after having been covalently bonded to the aforementioned polymer. As used herein, the terms "enzyme" and "enzyme molecule" are intended to describe peptide molecules having enzymatic activity for compounds deposited on contact lenses. These peptide molecules may include enzyme fragments and derivatives having enzyme activity, i.e. the ability to catalyze reactions such as the break down of proteins and lipids. These peptide molecules may be derived from a variety of sources including plant, animal, and bacteria. Examples of applicable enzymes include those commonly used in cleaning contact lenses. Specific examples include: proteases such as: subtilisin, papain, and pancreatin; lipases such as pancreas; as well as all classes of glycosidases, amylases, cellulases, and hemicellulases. As proteins and lipids are the most prevalent debris deposited on lenses, proteases and lipases are the most preferred classes of enzymes to be used in the subject conjugates. However, glycosidases and amylases in conjunction with proteases may provide good cleaning activity with respect to glycoproteins such as mucin.

With many conjugates it has been found that the enzyme activity of individual enzyme molecules may be reduced as a result of conjugate formation. Although some reduction in enzyme activity per enzyme molecule is acceptable, specific applications of the conjugate may limit the use of certain enzymes, or certain enzyme-polymer combinations.

The amount of conjugate used to clean a lens will depend upon the particular regimen, the polymer used, the number and types of enzyme molecules used and the overall enzyme activity of the conjugate. As a general guideline, the conjugate must have sufficient enzyme activity to remove deposits from a lens in the particular regime, typically a period of several minutes to several hours. Given that the subject conjugates are more easily rinsed away from the lens and can be less irritating to the eye, higher concentrations of enzymes, i.e. conjugates having higher enzyme activities may be used in many regimes to decrease the time required to clean the lens.

The particular enzyme and polymer used to form a desired conjugate will, in large measure, depend upon the specific application. For example, with hydrogel lenses, enzyme retention is believed to be primarily due to the enzyme penetrating the pores of the lens. Thus, the polymer used is such an application is believed to be serving primarily as a ballast group providing steric hindrance for enzyme penetration.

With most RGP lenses, enzyme interaction with the lens is believed to be largely ionic, hydrophobic, or a combination thereof Thus, the polymer chosen for the conjugate may include a similar charge as the lens surface. Furthermore, by using a polymer which is hydrophilic, adherence of the conjugate to the lens can be minimized.

In one embodiment, the subject enzyme-polymer conjugate comprises a watersoluble polymer chain having at least one, and more preferably a plurality of pendant enzyme molecules covalently bonded thereto. Such a conjugate may include different enzyme molecules covalently bonded to the same polymer chain. For example, the subject conjugate may include several different protease enzymes bonded thereto, e.g. subtilisin and papain; alternatively, the subject conjugate may include enzymes of different classes, e.g. proteases and lipases, thus providing a single cleaner capable of removing a variety of deposits.

In another embodiment, the subject conjugate comprises a single enzyme molecule having at least one, and preferably several water soluble polymers extending therefrom. For example, in one embodiment, the subject conjugate comprises an enzyme molecule having at least one polyalkylene oxide, e.g. polyethylene oxide, covalently bonded to the enzyme and extending therefrom. These conjugates are believed to be less irritating to the eye in addition to being more readily flushed from the eye.

A preferred method of cleaning contact lenses with the subject conjugates is to provide the conjugate in tablet form. Preparation of such tablets is the same as conventional enzyme tablet formation and is well known in the art. As with conventional enzyme tablets, the enzyme-polymer conjugate tablet is dissolved in several milliliters of an aqueous solution, e.g. a sterile saline solution, and a lens is soaked in the resulting solution. The soak time required for cleaning will vary from several minutes to several hours depending upon various factors previously described.

Another preferred method of cleaning contact lenses with the subject conjugates is to provide the conjugate in a liquid form, similar to conventional commercial liquid enzyme products. More specifically, the conjugate is preferably provided in a buffered aqueous solution. Such solutions should be stable and may require the use of glycerin or other species for providing enzyme stabilization as is common with liquid enzyme cleaners. However, its should be noted that the subject conjugates are generally more stabilized than the enzyme species unconjugated, and as such, use of enzyme stabilizers may be reduced or deemed unnecessary. In practicing the method, several drops of the liquid conjugate are dispensed into a small container, diluted with an aqueous solution, and the lens placed therein. Depending upon the concentration of the conjugate, a dilutent may also be added, e.g. saline, water, etc.

EXAMPLE 1

Soft hydrogel lenses were soaked in a phosphate buffered aqueous solution of radiolabelled subtilisin A and were compared with lenses soaked in a similar solution of a radiolabelled conjugate (i.e. subtilisin A and poly-L-lysine (PLL) having a molecular weight of approximately 500,000). Both solutions had an enzyme activity of approximately 100 PAU/ml. More specifically, two lenses were soaked in each of the respective solutions at ambient temperature with gentle rocking for about four hours. The lenses were subsequently removed from the solutions, blotted dry and the amount of radioactive enzyme on the lens was measured. The lenses were then rinsed with 3.0 ml of saline solution, after which the amount of radioactive enzyme was again measured. The lenses were subsequently placed in 3.0 ml of fresh saline solution and gently rocked for about one hour, after which the lenses were blotted dry and the amount of radioactive enzyme remaining on the lens was measured. The lenses were subsequently rinsed several more times after which the remaining radioactive enzyme remaining on the lens was measured.

The amount of conjugate remaining on the lens after initial soaking was significantly less than that of the subtilisin solution. Furthermore, the amount of conjugate remaining on the lens after subsequent rinsing was also significantly less than that of the corresponding subtilisin solution.

Based upon the foregoing, it should be apparent to those skilled in the art that the present invention is not limited by the examples set forth above and that the use of specific compositions can be determined from the specification without departing from the invention as herein disclosed and described. It should be understood that the scope of the present invention includes all modifications and variation that fall within the scope of the attached claims.

We claim:

1. A method for cleaning soft contact lenses comprising soaking the lenses in a solution comprising a water soluble enzyme-polymer conjugate characterized in that the enzyme-polymer conjugate comprises a water soluble polymer having a plurality of pendant enzyme molecules covalently bonded thereto.

2. The method of claim 1 wherein the enzyme-polymer conjugate comprises at least two different enzyme molecules covalently bonded to a water soluble polymer.

3. The method of claim 1 wherein the enzyme-polymer conjugate is provided in a tablet form, and wherein cleaning is achieved by dissolving the tablet within an aqueous solution and soaking the contact lenses therein.

4. The method of claim 1, wherein the enzyme-polymer conjugate is provided in a liquid form, and wherein cleaning is achieved by soaking the contact lenses in the liquid.

* * * * *